US00PP24979P3

(12) United States Plant Patent
Knight et al.

(10) Patent No.: US PP24,979 P3
(45) Date of Patent: Oct. 21, 2014

(54) CRAPEMYRTLE PLANT NAMED 'CREC-0030'

(50) Latin Name: *Lagerstroemia: L. indica×L. faurieiL. limii. 'Arapaho'×L. unknown*
Varietal Denomination: Crapemyrtle CREC-0030

(71) Applicants: Patricia R. Knight, Biloxi, MS (US); Wayne J. McLaurin, Poplarville, MS (US)

(72) Inventors: Patricia R. Knight, Biloxi, MS (US); Wayne J. McLaurin, Poplarville, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 13/573,604

(22) Filed: Sep. 27, 2012

(65) Prior Publication Data

US 2013/0104270 P1 Apr. 25, 2013

Related U.S. Application Data

(60) Provisional application No. 61/626,459, filed on Sep. 27, 2011.

(51) Int. Cl.
*A01H 5/00* (2006.01)
*A01H 5/02* (2006.01)

(52) U.S. Cl.
CPC ..... *A01H 5/02* (2013.01)
USPC ..... Plt./252

(58) Field of Classification Search
USPC ..... Plt./252
See application file for complete search history.

*Primary Examiner* — Kent L Bell
(74) *Attorney, Agent, or Firm* — Lawrence Arthur Schemmel

(57) ABSTRACT

A new and distinct cultivar of *Lagerstroemia* crapemyrtle plant named 'CREC-0030', characterized by its deep purple color flowers and small to medium growth habit.

4 Drawing Sheets

STATEMENT OF GOVERNMENT SUPPORT

This invention was made with government support under 58-6404-0-014 awarded by the U.S. Department of Agriculture Agricultural Research Service. The government may have certain rights in the invention.

Botanical classification: *Lagerstroemia: L. indica×L. faurieiL. limii*. 'Arapaho'×L. unknown.

Cultivar denomination: Crapemyrtle 'CREC-0030'.

BACKGROUND OF THE INVENTION

The present invention relates to a new and distinct cultivar of the ornamental flowering shrub and landscape plant of the genus *Lagerstroemia*, commonly known as crapemyrtle, of the family Lythraceae, and is referred to hereinafter by its cultivar denomination 'CREC-0030'. This novel plant is an asexually propagated hybrid of crapemyrtle that was selected in 2008 from approximately 2800 crosses. The female seed parent is *Lagerstroemia indica×L. faurieiL. limii*. 'Arapaho' (PI 633034). The male pollen parent is unknown since the new cultivar resulted from open pollination of 'Arapaho'. 'CREC-0030' was selected for its unique deep purple flower color and small to medium size. The designation 'CREC-0030' was evaluated under the experimental number '2008-0030' and experimental name 'CREC-0030'. This high quality novel and distinct cultivar of crapemyrtle plant was vegetatively propagated in Poplarville, Miss. using vegetative medial cuttings, as opposed to tip cuttings, taken from semi-hard, current season's growth. Stem diameters were approximately ⅛ to ¼ inch. Each of several generations of cuttings has produced stable plants identical to the original seedling plant.

SUMMARY OF THE INVENTION

The new cultivar is a *Lagerstroemia* hybrid resulting from the open pollination of *Lagerstroemia: L. indica×L. faurieiL. limii*. 'Arapaho' (female parent). 'CREC-0030' is a distinctive, new cultivar of crapemyrtle plant characterized by its deep purple flower color and small to medium crapemyrtle growth habit. The traits of the new plant are continually maintained when propagated asexually. This new cultivar may vary slightly with changes in location, temperature, light, and other environmental conditions, but the genotype will not be affected. 'CREC-0030' also exhibits the quality and characteristic of adaptability to all areas of hardiness zones 7-10, based on observed temperatures at the growing locations compared to the USDA Hardiness Zone map. 'Arapaho', the female parent of 'CREC-0030', is a tall crapemyrtle compared to the small to medium size of 'CREC-0030'. 'Arapaho' also has red flowers compared to deep purple flowers for 'CREC-0030'. Comparison between the closest crapemyrtle cultivar to the new plant shows that, utilizing USDA National Arboretum data, 'Powhatan' is also an 8 to 10-foot crapemyrtle which is a dense shrub with parentage of indicia, unlike the cross of the new cultivar. Moreover, the new plant is larger than 'Powhatan'. This new plant has unique flower color contained in a small to medium growing crapemyrtle. The combination of 'CREC-0030's purple flower color and small to medium growth habit distinguishes it from all other crapemyrtle cultivars known to the inventors.

BRIEF DESCRIPTION OF THE DRAWINGS

The color photographs of FIG. 1 through FIG. 4 illustrate the overall appearance and unique characteristic of purple flower color of the new crapemyrtle cultivar 'CREC-0030'. The photographs were taken using conventional techniques and, although colors may appear different from actual colors due to light reflectance, the new plant and its colors are shown as true and accurately as reasonably possible by conventional photographic techniques. Colors in the photographs may differ from the actual colors and values in the description of the new crapemyrtle plant due to light conditions and other factors. The photographs and the detailed description of the invention are intended to illustrate further the invention and its advantages.

DETAILED BOTANICAL DESCRIPTION OF THE VARIETY

Latin name: *Lagerstroemia*×'CREC-0030'

*Lagerstroemia: L. indica*×*L. faurieiL. limii*. 'Arapaho'× *Lagerstroemia* unknown Cultivar denomination: 'CREC-0030'

The present invention is a novel *Lagerstroemia*×'CREC-0030' cultivar known as 'CREC-0030' that is different from other crapemyrtle cultivars.

ARP X VEL 0030 Row 14—Replication 2—Plant # 15 in Rep. McNeill planting.

The following is a detailed botanical description of the characteristics of the new *Lagerstroemia* crapemyrtle cultivar known as 'CREC-0030', based on observations of the plant grown at Poplarville, Miss., and under similar conditions to those for growing these plants commercially. 'CREC-0030' has been observed under many but not all possible environmental conditions. Color notations of plant tissues are based upon The Royal Horticultural Society (R.H.S.) Colour Chart, 2001 Edition. Color notations may have been slightly affected by light quality and fertility and general plant growth. Certain characteristics will vary depending on the age of the plants so that dimensions, sizes, and colors are approximations or averages since the cultivar has not been observed under every possible environmental condition. Therefore the phenotype of the cultivar may differ from the descriptions depending upon environmental variations including, but not limited to, the season, temperatures, day lengths, light direction and quality, and fertilization, as well as other factors.

The present invention is a *Lagerstroemia* hybrid resulting from the open pollination of *Lagerstroemia indica*×*L. faurieiL. limii*. 'Arapaho' (female parent), whereby 'Arapaho' was crossed with a *Lagerstroemia* unknown pollen donor (male parent). The stem color of this new plant is Royal Horticultural Society (R.H.S.) Colour Chart Group 199-B. The average total height is 8.4 feet, soil to first branch average is 24.2 inches, and the first branch to tip average is 63.2 inches. The average caliper at 6 inches is 0.84 inches, average stem length at 3 inches is 61.67 inches, and the average yearly growth is 44.60 inches. The average stem caliper at 3 inches is 0.70 inches and the average internode length is 1.35 inches, although internode lengths are subjective since they depend on factors such as sun exposure, nutrition, pruning, and the like. Stem texture is smooth to exfoliating. The leaf top color is R.H.S. Colour Chart Group 139-A. The flower petal color is deep purple (R.H.S. Colour Chart Group N72-A). This new plant is a crapemyrtle with unique deep purple flower color that may be used as a specimen in landscapes where crapemyrtles are traditionally used. This crapemyrtle plant will be in the twelve to fifteen (12-15+) foot plus range for growth. Currently, not many crapemyrtles exist that are "deep purples" like the present invention and that are in this growth range known to the inventors.

Figure 1:
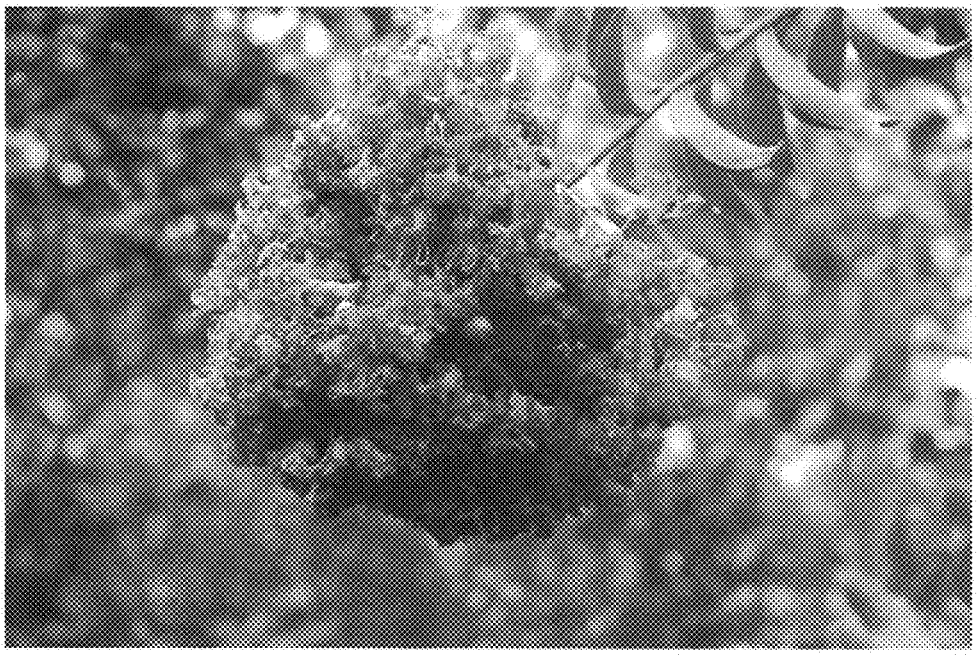
FIG. 1 is a color photograph of the new crapemyrtle 'CREC-0030' taken at Poplarville, Miss. that shows the flower and leaf color of the new cultivar.
Figure 2:
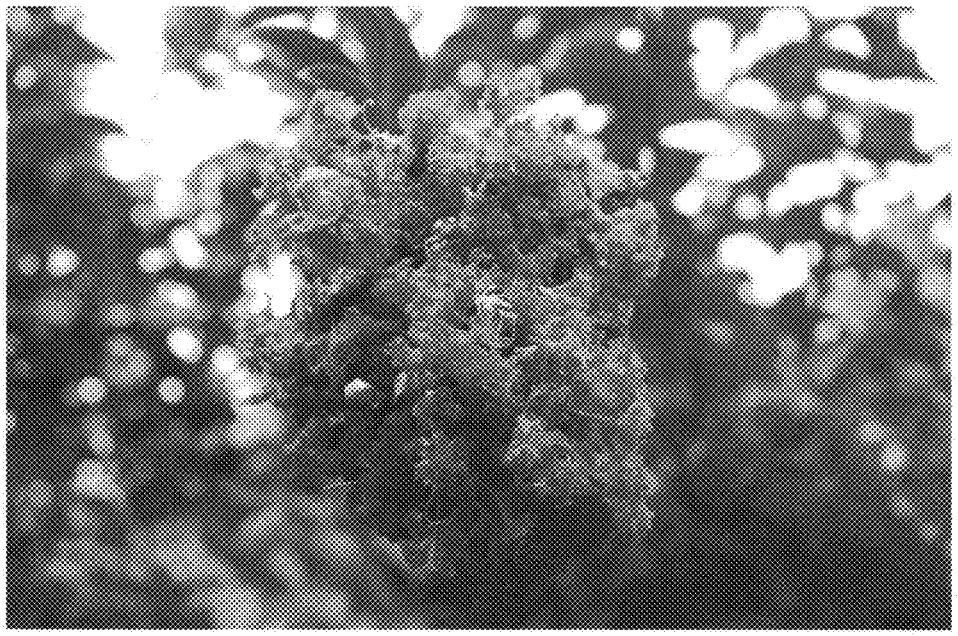
FIG. 2 is a color photograph of the new crapemyrtle 'CREC-0030' taken at Poplarville, Miss. that shows the flower and leaf color of the new cultivar.
Figure 3:
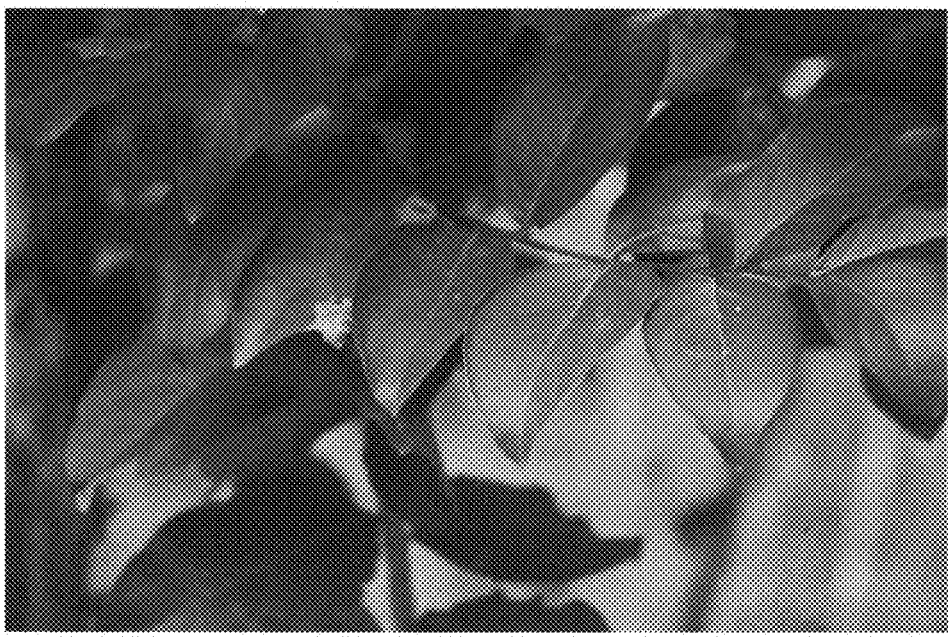
FIG. 3 is a color photograph of the new crapemyrtle 'CREC-0030' taken at Poplarville, Miss. that illustrates leaf and stem color of the new plant.
Figure 4:
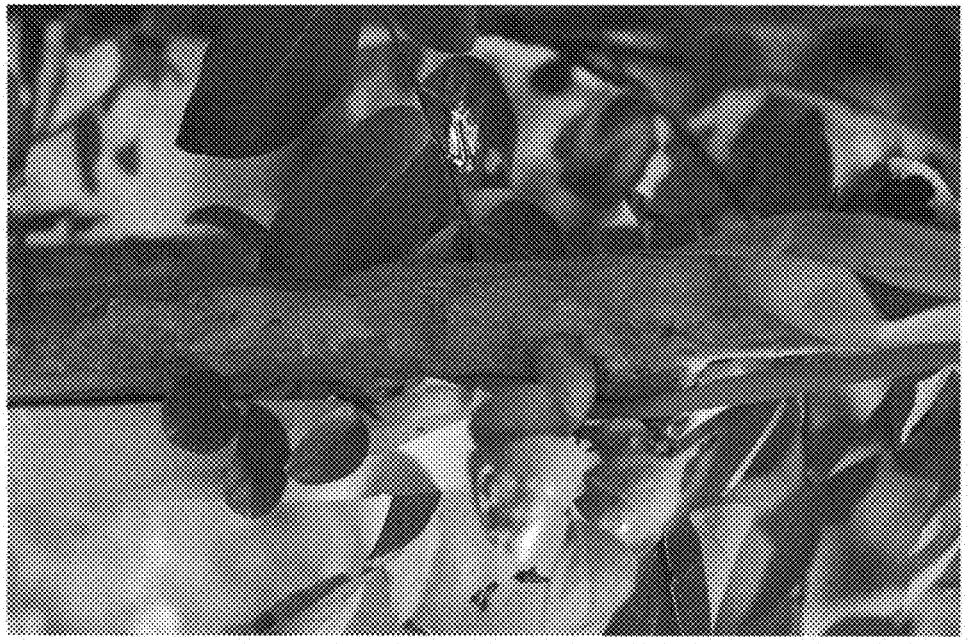
FIG. 4 is a color photograph of the new crapemyrtle 'CREC-0030' taken at Poplarville, Miss. that illustrates leaf and stem color of the new plant.

FIGS. 1 and 2 show the flower color and the leaf color of the new cultivar. FIG. 3 shows the stem color of the new cultivar. FIG. 4 shows the leaf color and stem color of the new plant.

The final height and width of the plant have not been observed. Three-year plants in the research facility are greater than 12 to 15 feet tall and approximately 6 to 8 feet wide, forming a multiple or single trunk small to medium crapemyrtle. The new plant has outer mature bark color in the grey-brown group in R.H.S. Colour Chart Group 199-D and inner mature bark color in the grey-brown group in R.H.S. Colour Chart Group 199-C. New stem growth is in the greyed-purple group in R.H.S. Colour Chart Group 183-A. It can possibly be grown as a medium shrub in climates where shoot growth is killed to the ground each winter. Its foliage comprises glossy green leaves that are opposite and that are approximately from 2.00 to 2.50 inches in length and from 1.00 to 1.50 inches in width. The leaf top color is R.H.S. Colour Chart Group 139-A. The leaf underside color is R.H.S. Colour Chart Group 146-A. The leaf type is simple and is persistent and deciduous. The leaf margin is entire, the leaf shape is ovate to elliptical, and the leaf venation is pinnate. The leaf apex is acuminate, the leaf base is rounded, and the overall shape is ovate to elliptical. New leaf color is in the green group in R.H.S. Colour Chart Group 137-C and the new leaf mid-vein color is in the greyed-purple group in R.H.S. Colour Chart Group 183-B. The stem is rather slender with a slightly angular shape with slight wings when young and a round shape when growth is more mature. The new plant is a deciduous, summer-flowering plant, so that fall color has been inconsequential. The plant has shown insect and disease tolerance comparable to the parent under field conditions.

The flowers are perfect, 6-petaled and each flower is approximately 1.25 inches in diameter. The flowers are purple and are most typically visible from early June to late August depending on environmental conditions. Flower color represents the closest impression of the entire florescence. Individual florets are very small, so the overall impression is the observed characteristic. The flower petal color is R.H.S. Colour Chart Group N72-A. The flowers have medium tapered panicles. The flower panicle is approximately 10 inches long. The unopened flower capsule color is R.H.S. Colour Chart Group 59-A. When the flowers fade, they generally fade to lighter shades of purple, lavender, or light blue, and not to pink or red tones.

The fruit is comprised of seed pods that are dark green in color turning to brown, a mature seed pod color that is R.H.S.

Colour Chart Group 144-A. The fruit is a broad-ellipsoidal 6-valved dehiscent capsule, brown in color in R.H.S. Colour Chart Group 144-A, approximately ½ of an inch wide. Seeds are approximately ⅜ to ½ of an inch long and winged. The pistil color is R.H.S. Colour Chart Group 14-A. A woody capsule generally persists on the panicle until late winter. Cold testing in the laboratory for cold hardiness has not yet been completed for the new cultivar. Plants had just begun to exhibit the exfoliating bark characteristics common to crapemyrtles at the time of observation.

Rooting of the new small to medium-sized crapemyrtle is easily accomplished, making the plant excellent for production purposes, and such rooted plants are identical to the original. The novelty of the plant includes its purple flower color (R.H.S. Colour Chart Group N72-A) and its small to medium size. 'CREC-0030' may be used as a specimen in landscapes where crapemyrtles are traditionally used. The new crapemyrtle plant will be in the 15-foot range for growth. Currently, not many crapemyrtles exist that are this "deep purple" color and that are in this small to medium crapemyrtle growth range group.

As will be apparent to those skilled in horticultural science, the new and distinct crapemyrtle plant cultivar described herein may vary in minor detail due to climatic, soil, and cultural conditions under which the variety may be grown, as well as the stage of growth.

What is claimed is:

1. A new and distinct cultivar of crapemyrtle *Lagerstroemia* hybrid plant named 'CREC-0030', substantially as herein illustrated and described.

* * * * *